United States Patent [19]

Lawrence

[11] Patent Number: 5,735,061
[45] Date of Patent: Apr. 7, 1998

[54] AUTOCLAVING PROCESS AND APPARATUS

[75] Inventor: Peter David Lawrence, Brisbane, Australia

[73] Assignee: Electrical Control Systems Pty. Ltd., Thornsland, Australia

[21] Appl. No.: 648,200

[22] PCT Filed: Nov. 25, 1994

[86] PCT No.: PCT/AU94/00727

§ 371 Date: May 24, 1996

§ 102(e) Date: May 24, 1996

[87] PCT Pub. No.: WO95/14494

PCT Pub. Date: Jun. 1, 1995

[30] Foreign Application Priority Data

Nov. 26, 1993 [AU] Australia ................. PM2664

[51] Int. Cl.⁶ ........................................ F26B 3/00
[52] U.S. Cl. ........................ 34/493; 34/552; 422/295
[58] Field of Search ........................ 34/92, 73, 77, 34/403, 408, 406

[56] References Cited

U.S. PATENT DOCUMENTS

| | | | |
|---|---|---|---|
| 3,481,692 | 12/1969 | Linder | 422/112 |
| 3,661,505 | 5/1972 | Frolich | 422/3 |
| 3,721,527 | 3/1973 | Lodige et al. | 422/36 |
| 3,904,361 | 9/1975 | Egger | 422/27 |
| 4,239,730 | 12/1980 | Fahlvik et al. | 422/109 |
| 4,622,800 | 11/1986 | Turtschan | 53/425 |
| 4,637,916 | 1/1987 | Henebert et al. | 422/36 |
| 5,196,165 | 3/1993 | Harrell et al. | 42/110 |

FOREIGN PATENT DOCUMENTS

| | | |
|---|---|---|
| B-55131/86 | 8/1986 | Australia . |
| 1042622 | 11/1978 | Canada . |
| 0 096 139 | 12/1983 | European Pat. Off. . |
| 1 555 295 | 11/1979 | United Kingdom . |
| 2 131 695 | 6/1984 | United Kingdom . |

*Primary Examiner*—Henry A. Bennett
*Assistant Examiner*—Pamela A. O'Connor
*Attorney, Agent, or Firm*—DeLio & Peterson, LLC

[57] ABSTRACT

Apparatus and process for sterilizing and drying products comprising a first step of autoclaving and a second step of cyclic pressurizing with a substantially dry contaminant-free gas. The second step obviates the problem of recontamination after sterilization and permits drying at lower than conventional temperatures.

15 Claims, 1 Drawing Sheet

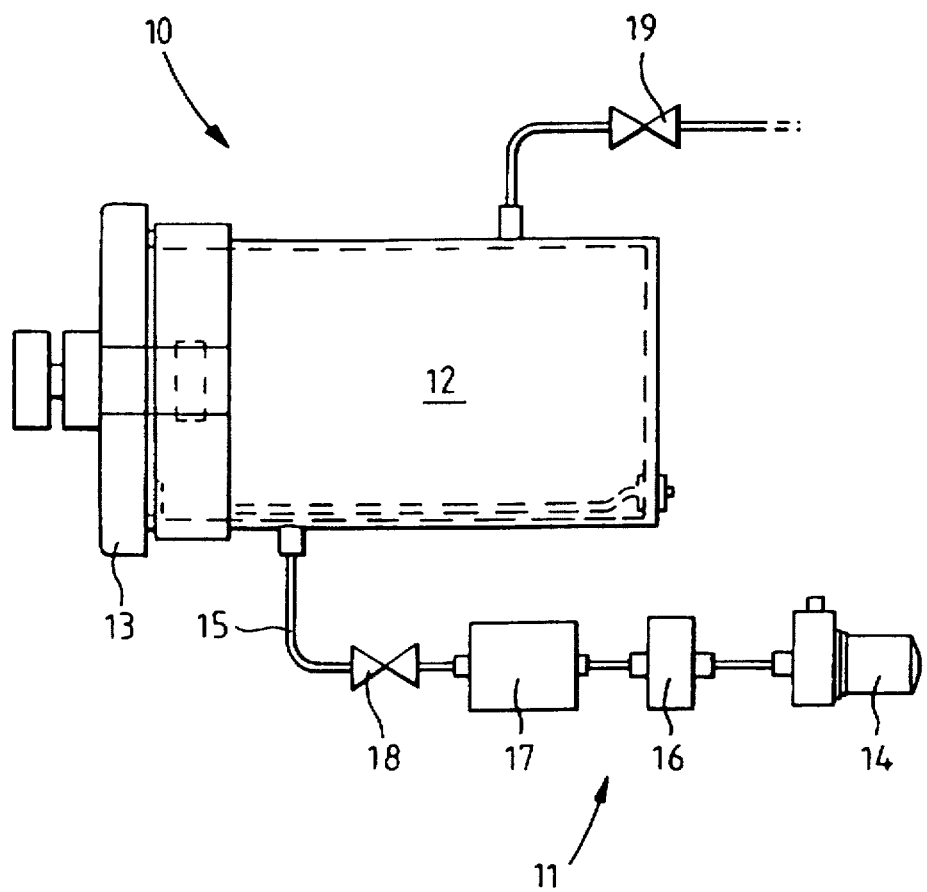

AUTOCLAVING PROCESS AND APPARATUS

BACKGROUND OF THE INVENTION

This invention relates to apparatus and processes for sterilizing products using saturated steam, followed by the drying thereof. The invention is particularly concerned with ensuring that the products are cost effectively and efficiently dried without the possibility of recontamination during the drying stage.

DESCRIPTION OF PRIOR ART

Conventionally, products are sterilized and dried in an autoclave by a process which basically comprises subjecting the products to saturated steam at elevated pressure followed by the application of a vacuum to remove the water. The vacuum is applied in a single step while heating, after which the autoclave is vented to the atmosphere.

A typical problem with such a system is the potential for recontamination of the sterilized products should the autoclave leak for any reason as in that case air-borne microorganisms can be readily introduced into the autoclave by virtue of the below atmospheric pressure existing therein. Another disadvantage is the necessity to employ relatively expensive vacuum pumps to produce the required pressure reductions for effective vacuum drying. Such vacuum pumps also add considerably to the total time required to sterilize and dry a product.

One proposal to overcome the former of these problems is to reduce the degree of vacuum whilst streaming filtered, preferably heated, air through the autoclave. This, however, considerably reduces the drying effectiveness by further increasing the time required to achieve a suitable degree of drying. It also does not address the problems associated with vacuum pumps.

OBJECT OF THE INVENTION

It is therefore an object of the present invention to provide an apparatus and process which obviates or at least minimises these problems and which provides the public with a useful alternative.

SUMMARY OF THE INVENTION

According to one aspect of the present invention there is provided an apparatus for sterilizing and drying products, said apparatus comprising:

(i) a sterilizing/drying chamber, (ii) means for supplying saturated steam under pressure to the chamber in order to effect the sterilization of products placed therein, (iii) means for supplying gas under pressure to the chamber for drying of products placed therein, said gas being essentially dry and completely contaminant free, (iv) access means to the chamber for products to be sterilized and dried, (v) vent means in the chamber to enable venting of the saturated steam and pressurized gas, and (vi) control means whereby the saturated steam used to sterilize products contained in the chamber, and the subsequential cycling of gas under pressure into and out of the chamber, is effectively regulated.

The apparatus is particularly adapted for small scale use such as the sterilization and drying of instruments in doctors and dentists surgeries. However, it will be readily appreciated by the skilled addressee that the apparatus can be scaled up to large scale industrial use within the parameters of the defined inventive concept. Such large scale use is exemplified by the sterilization and drying of grain products on a continuous throughput system.

Automation and control of the apparatus can likewise be effected by the application of common general knowledge and the use of appropriately adapted hardware incorporating microprocessors and the like, and specially configured software packages. None of these criteria impinge upon the broad inventive considerations made by the inventor and disclosed herein.

DETAILED DESCRIPTION OF THE INVENTION

The means for supplying gas under pressure to the chamber for drying products placed therein will normally be a compressor however supply may alternatively be made from a gas cylinder or gas generation apparatus. Generally, the pressure of the gas will be in the range of 1 to 100 kPa, most preferably around 80 kPa. Higher pressures are preferred as these reduce the number of cycles required to dry the product. This may be particularly important for porous products. Suitably, in each pressurizing and release cycle, the pressure is maintained for a sufficient period to at least partially equilibrate before being released to atmospheric pressure.

Preferably, the gas pressurizing process is effected in short bursts of between about ten and sixty seconds, and the pressure release is fast and continues until the chamber is substantially depressurized. The drying cycles can continue for periods of up to ten or more minutes depending upon the nature of the article being dried.

The rapid venting of the drying chamber can be achieved by opening a relatively large port in the chamber to the atmosphere. Generally, the rate of pressure reduction brought about by venting will be extended over a sufficient period of time to correspond with the pressurization phase.

Since such pressure reduction will be accompanied by a drop in temperature of the gas/water vapour remaining in the chamber, it is suitably regulated to enable heat transfer from an external heat source or the residual heat of the product to the gas remaining to prevent the system from progressing to a condensing atmosphere within the chamber. The progressive uptake of heat by a gradual reduction in pressure also maximises the moisture carrying capacity of the gas and hence promotes moisture carry through.

Generally, the gas is heated prior to admission to the chamber, by passing it through a heat exchanger or other conventional heating arrangement such as an electrical heating element. Alternatively, heating may be effected by internal exchange with waste heat vented from the chamber.

Heating is generally carried out within the temperature range of 110° to 150° C. Further pretreatment of the gas may be effected by dehumidification, for example by refrigeration, to reduce any entrained water in the gas to minimal amounts. Thus, for instance, the gas can be subjected to flow through a heat pump apparatus wherein the evaporator portion of the apparatus effects the condensation out of airborne moisture and wherein the condenser side of the apparatus effects the heating of the cooled air.

Although heating is generally preferred, it is not essential and, in fact, it can be undesirable in some instances. Thus, in the case of temperature sensitive items such as, for instance, some types of dental handpieces, it is imperative that cold drying be carried out. Such cold drying can be effectively and efficiently performed within the stated parameters of the invention.

A gas filter is preferably employed to remove particles down to about 5 microns in diameter from the drying gas such that any airborne contaminants are effectively removed. The filter can be chosen from a wide range of commercially available equipment and will be selected according to the size and purpose to which the sterilizing/drying chamber is to be put. Thus, for the small scale treatment of products such as surgical and dental equipment, a high efficiency particulate gas filter is particularly appropriate.

The control means is designed to effect the necessary supply of steam to the sterilizing chamber followed by the regulation of the gas cyclic purging steps until the proper degree of drying has been achieved. Where appropriate, control will also be effected over any filter means present as well as any heating and/or dehumidifying of the purge gas. Suitably, the control means is responsive to and includes sensing means adapted to monitor the physical variant parameters such as pressure, temperature and humidity. For instance, the process may be cycled for a number of times depending on a measurement of the temperature and humidity of the gas exhausted from the chamber while heating means responsive to the sensing means may be operated to maintain temperatures in the chamber and/or in the incoming gas stream to within selected predetermined limits.

The gas used to pressurize the system can be any of a wide range of gases. The preferred gases are those with high specific heat capacities, which are nonreactive and inexpensive. Air is the preferred gas, but nitrogen or mixtures of air and nitrogen, or other inert gases may be effectively used.

Another aspect of the invention comprises a process for sterilizing and drying a product, said process comprising the steps of:

(i) subjecting the product in a closed system to saturated steam under pressure for a sufficient time to sterilize the product, (ii) venting the system to the atmosphere, (iii) subjecting the product in the closed system to a substantially dry contaminant-free gas at an elevated pressure, (iv) venting the system to the atmosphere, and (v) repeating steps (iii) and (iv) in a cyclic sequence until the product has reached an acceptable state of dryness.

DESCRIPTION OF PREFERRED EMBODIMENT

A preferred embodiment of the invention is illustrated in the attached drawing, FIG. 1. This drawing is a schematic representation of an autoclave 10 having an associated drying system according to the present invention. The means for supplying saturated steam under pressure, and peripheral accompaniments, are omitted for clarity as these can be conventional arrangements and do not in any way qualify or modify the inventive concept which resides in the drying technique per se.

The autoclave comprises a chamber 12 into which articles to be sterilized are placed by way of a pressure sealed door 13 with locking mechanism.

Means for supplying air under pressure to the chamber comprises an air pump or compressor 14 which injects the air by way of high pressure air line 15. Prior to entering the chamber 12, the air passes through an in-line high efficiency particulate air filter 16 which removes entrained air particles down to a size of approximately 5 microns in diameter. This is sufficient to remove all known air-borne pathogens and thereby ensures that the air is sterile.

Upon passing through the air filter 16, the air travels to the optional heat exchanger 17 where it is heated to a degree which maximises its drying ability. Control means incorporating a check valve 18 regulates the cyclic flow of heated air under pressure into the chamber 12, in unison with vent valve 19 by way of which the chamber is vented at predetermined intervals until the articles within the chamber have been dried to an acceptable amount.

A practical example of a sterilization and drying process using this equipment will now be given.

EXAMPLE

Linen fabric weighing approximately 400 g was placed in the autoclave chamber 12. This chamber had a volumetric capacity of approximately 9 liters. Sterilizing was accomplished by generation of saturated steam within the housing and holding a pressure of 200 kPa and temperature of 134° C. for about four minutes and then released to 0 kPa.

The pressure is the chamber 12 was then raised to approx 80 kPa by pumping heated air from the compressor 14 via heat exchange 17 into the chamber; this process taking approx 30 seconds. The pressure was then reduced to 0 kPa and then immediately raised again to the earlier conditions. This cyclic process was continued for ten minutes to substantially dry the load.

Several tests of the drying cycle of the present invention were conducted as follows:
TEST 1

The external surface of the autoclave chamber 12 was controlled at 50° C. Air was pumped through the heat exchanger 17 and into the chamber at 150° C. Pumping continued until the pressure of the chamber reached 100 kPa, and was then released immediately by opening exhaust valve 19 in the chamber. This was repeated for short periods.

It was found that such a process achieved enhanced drying and faster temperature increases in the load.
TEST 2

Larger dense linen packs were introduced into the autoclave chamber 12. This chamber had a volumetric capacity of approximately 40 liters. A diaphragm compression pump 14 having an output capacity of 62 liters per minute was used to pressurize the chamber. The humidity of the air was 82%. Steam was generated in the chamber displacing the majority of the air and the steam was then discharged from the chamber and the drying process commenced. Heated air was pumped into the chamber until the pressure was raised to 90 kPa, taking approx 30 seconds and held at 90 kPa for approx 30 seconds. The pressure was then released until 0 kPa was attained in the chamber. This cycle was repeated 15 times. The monitored cyclic decrease in temperature as those recorded indicate that an enhanced evaporative effect is taking place within the load each time the pressure is released. This led to shortened drying times for the load.

It is considered that rapid short pressure pulses are most effective when the drying method is used on existing equipment.

Small capacity compressors will take longer to achieve the desired elevated pressures. This may result in the air remaining in the chamber too long resulting in a condensing atmosphere. However utilizing a large capacity compressor to achieve higher pressures rapidly may increase the overall performance but the cost of larger capacity compressors may be commercially prohibitive. Accordingly it is preferred to use an intermediate sized compressor able to be operated so as to avoid a condensing atmosphere to provide a compromise between efficiency and cost.

It will of course by realised that while the above has been given by way of illustrative example of this invention, all such and other modifications and variations thereto as would be apparent to persons skilled in the art are deemed to fall within the broad scope and ambit of this invention as is herein set forth.

I claim:

1. An apparatus for sterilizing and drying products, said apparatus comprising:
   (i) a sterilizing/drying chamber,
   (ii) means for supplying saturated steam under pressure to the chamber in order to effect the sterilization of products placed therein,
   (iii) means for cycling gas under pressure to the chamber for drying of products placed therein, said gas being essentially dry and completely contaminant free,
   (iv) access means to the chamber for products to be sterilized and dried,
   (v) vent means in the chamber to enable venting of the saturated steam and pressurized gas, and
   (vi) control means for regulating the saturated steam used to sterilize products contained in the chamber, and the subsequential cycling of the drying gas under pressure into and out of the chamber, said control means adapted to admit the drying gas to the chamber in bursts of between 10 and 60 seconds with sequential rapid venting until essentially complete depressurization has occurred, such cycling of the drying gas continuing until an acceptable state of dryness is produced in the products placed in the chamber.

2. An apparatus for sterilizing and drying products as claimed in claim 1, wherein the means for supplying gas under pressure to the chamber for drying of products placed therein is a compressor.

3. An apparatus for sterilizing and drying products as claimed in claim 2 and wherein the gas supplied under pressure to the chamber is heated in a heat exchanger prior to admission to the chamber to a temperature within the range of 110° –150° C.

4. An apparatus for sterilizing and drying products as claimed in claim 1 and wherein the gas supplied under pressure to the chamber is heated in a heat exchanger prior to admission to the chamber to a temperature within the range of 110° –150° C.

5. An apparatus for sterilizing and drying products as claimed in claim 1, wherein contaminants are removed from the gas supplied under pressure to the chamber by filtering the gas through a filter before it is admitted to the chamber, said filter having a pore diameter of less than 5 microns.

6. An apparatus for sterilizing and drying products as claimed in claim 1, wherein the gas supplied under pressure to the chamber is dehumidified before it is admitted to the chamber.

7. An apparatus for sterilizing and drying products as claimed in claim 1, wherein the gas supplied under pressure to the chamber for drying of products placed therein, is air.

8. An apparatus for sterilizing and drying products as claimed in claim 1, wherein the pressure of gas supplied to the chamber for drying of products placed therein, is within the range of 1 to 100 kPa.

9. An apparatus for sterilizing and drying products as claimed in claim 1 and including sensor means whereby the moisture content of the products, exhausted gas, or the chamber is sensed to indicate the progress of the drying process.

10. A process for sterilizing and drying a product, said process comprising the steps of:
    (i) subjecting the product in a closed system to saturated steam under pressure for a sufficient time to sterilize the product,
    (ii) venting the system to the atmosphere,
    (iii) subjecting the product in the closed system to a substantially dry contaminant-free gas at an elevated pressure for a period of between 10 and 60 seconds,
    (iv) rapidly venting the system to the atmosphere until the closed system is substantially depressurized, and
    (v) repeating steps (iii) and (iv) in a regulated cyclic sequence until the product has reached an acceptable state of dryness.

11. A process for sterilizing and drying a product as claimed in claim 10, wherein the substantially dry contaminant-free gas is heated prior to admission to the closed system, to a temperature within the range of 110° to 150° C.

12. A process for sterilizing and drying a product as claimed in claim 10, wherein the substantially dry contaminant-free gas is filtered prior to admission to the closed system to remove any contaminants therein.

13. A process for sterilizing and drying a product as claimed in claim 10, wherein the elevated pressure of the substantially dry contaminant-free gas is within the range of 1 to 100 kPa.

14. A process for sterilizing and drying a product as claimed in claim 10, wherein steps (iii) and (iv) are continued for a period of up to ten minutes.

15. A process for sterilizing and drying a product as claimed in claim 10, wherein the venting of the system to atmosphere in step (iv) is selected to permit heat transfer from an external heat source, or the residual heat of the product to the gas remaining to prevent a condensing atmosphere forming in the closed system.

* * * * *